(12) United States Patent
Kawaura et al.

(10) Patent No.: US 10,292,731 B2
(45) Date of Patent: May 21, 2019

(54) MEDICAL TUBE, MEDICAL TUBE ASSEMBLY AND PUNCTURE NEEDLE

(71) Applicant: TERUMO KABUSHIKI KAISHA, Shibuya-ku, Tokyo (JP)

(72) Inventors: Masakatsu Kawaura, Sunnyvale, CA (US); Nao Yokoi, Sunnyvale, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 368 days.

(21) Appl. No.: 14/633,469

(22) Filed: Feb. 27, 2015

(65) Prior Publication Data
US 2015/0164549 A1    Jun. 18, 2015

Related U.S. Application Data

(63) Continuation of application No. PCT/JP2012/071593, filed on Aug. 27, 2012.

(51) Int. Cl.
*A61B 17/34* (2006.01)
*A61F 2/00* (2006.01)
(Continued)

(52) U.S. Cl.
CPC ...... *A61B 17/3468* (2013.01); *A61B 17/0469* (2013.01); *A61B 17/3421* (2013.01);
(Continued)

(58) Field of Classification Search
CPC ............ A61B 17/3468; A61B 17/3421; A61B 17/0469; A61B 17/06066;
(Continued)

(56) References Cited

U.S. PATENT DOCUMENTS 6,423,080 B1    7/2002 Gellman et al.
2002/0077526 A1    6/2002 Kammerer et al.
(Continued)

FOREIGN PATENT DOCUMENTS

JP    2001-511684 A    8/2001
JP    2005-514967 A    5/2005
(Continued)

OTHER PUBLICATIONS

Extended European Search Report dated Feb. 17, 2016, by the European Patent Office in corresponding European Patent Application No. 12883448.8-1659. (10 pages).
(Continued)

*Primary Examiner* — Kaylee R Wilson
(74) *Attorney, Agent, or Firm* — Buchanan Ingersoll & Rooney PC

(57) ABSTRACT

A medical tube is disclosed, which is configured to have an elongated implant inserted in the medical tube. The medical tube includes a tube having a proximal end opening where the tube is open at a proximal end of the tube. The tube can include a bent region where an intermediate portion in the longitudinal direction of the tube is bent and where a bent state is maintained, and a connection portion which is provided near the proximal end opening and to which a puncture needle having a sharp needle tip at a distal end of the puncture needle is connected from a needle tip side.

18 Claims, 17 Drawing Sheets

(51) Int. Cl.
*A61B 17/00* (2006.01)
*A61B 17/04* (2006.01)
*A61B 17/06* (2006.01)

(52) U.S. Cl.
CPC .. *A61F 2/0063* (2013.01); *A61B 2017/00805* (2013.01); *A61B 2017/0608* (2013.01); *A61B 2017/06052* (2013.01); *A61B 2017/06104* (2013.01); *A61B 2017/3409* (2013.01); *A61F 2/0045* (2013.01); *A61F 2002/0072* (2013.01); *A61F 2250/0071* (2013.01); *F04C 2270/0421* (2013.01)

(58) Field of Classification Search
CPC .. A61B 2017/3409; A61B 2017/06104; A61B 2017/06052; A61B 2017/00805; A61B 2017/0608; A61F 2/0063; A61F 2/0045; A61F 2250/0071; A61F 2002/0072; F04C 2270/0421
See application file for complete search history.

(56) References Cited

U.S. PATENT DOCUMENTS

| | | | | |
|---|---|---|---|---|
| 2002/0091373 | A1* | 7/2002 | Berger | A61B 17/0482 606/1 |
| 2002/0099258 | A1* | 7/2002 | Staskin | A61B 17/0482 600/29 |
| 2003/0004395 | A1* | 1/2003 | Therin | A61F 2/0045 600/37 |
| 2004/0087970 | A1 | 5/2004 | Chu et al. | |
| 2004/0102808 | A1* | 5/2004 | Voss | A61B 17/0483 606/223 |
| 2004/0153008 | A1* | 8/2004 | Sharf | A61B 5/0031 600/588 |
| 2006/0195010 | A1* | 8/2006 | Arnal | A61B 17/06066 600/30 |
| 2007/0123746 | A1 | 5/2007 | MacLean | |
| 2011/0046436 | A1* | 2/2011 | Sokol | A61F 2/0045 600/30 |
| 2012/0158009 | A1 | 6/2012 | Ostrovsky et al. | |

FOREIGN PATENT DOCUMENTS

| | | |
|---|---|---|
| JP | 2006-517115 A | 7/2006 |
| JP | 2010-099499 A | 5/2010 |
| WO | 97/47246 A1 | 12/1997 |
| WO | WO 98/35616 A1 | 8/1998 |
| WO | WO 02/098322 A1 | 12/2002 |
| WO | WO 2003/075792 A1 | 9/2003 |
| WO | WO 2004/016196 A2 | 2/2004 |
| WO | 2005/122954 A1 | 12/2005 |

OTHER PUBLICATIONS

International Search Report (PCT/ISA/210) dated Nov. 13, 2012, by the Japan Patent Office as the International Searching Authority for International Application No. PCT/JP2012/071593.

* cited by examiner

F I G . 1 4
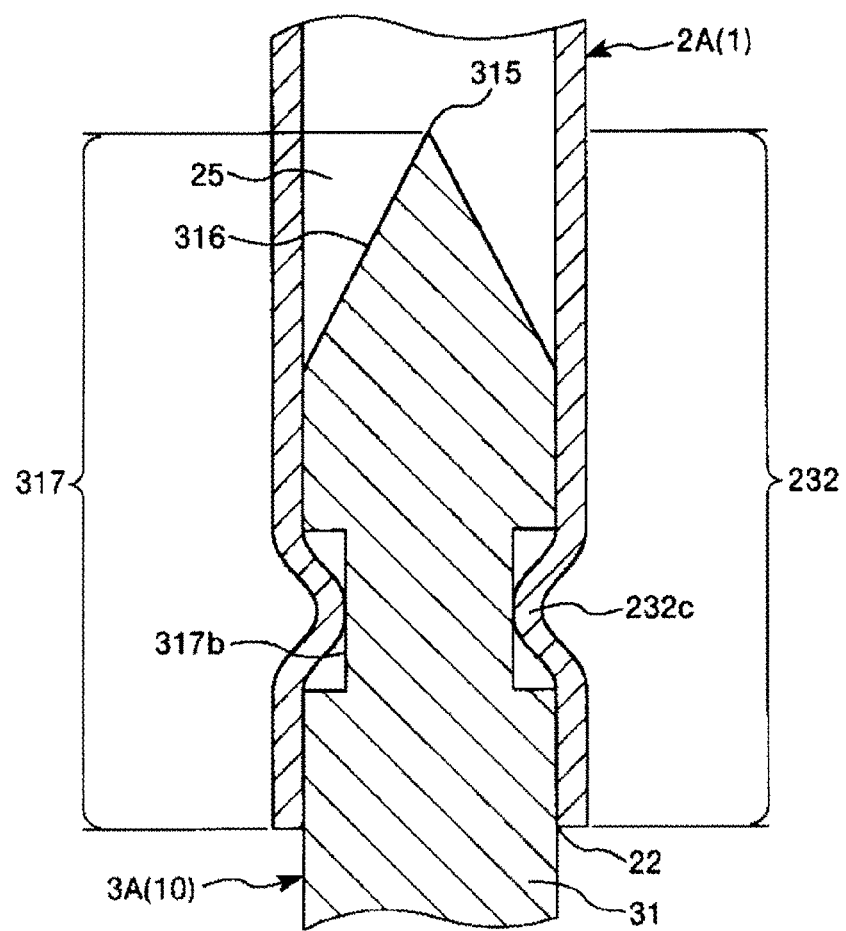

US 10,292,731 B2

MEDICAL TUBE, MEDICAL TUBE ASSEMBLY AND PUNCTURE NEEDLE

RELATED APPLICATION(S)

This application claims priority as a continuation application under 35 U.S.C. § 120 to PCT/JP2012/071593 filed as an International Application on Aug. 27, 2012 designating the U.S., the entire content of which is hereby incorporated by reference in its entirety.

FIELD

The present disclosure relates to a medical tube, a medical tube assembly and a puncture needle.

BACKGROUND INFORMATION

If a person suffers from a urinary incontinence, specifically if a person suffers from a stress urinary incontinence, then urine leakage can be caused by application of abdominal pressure during normal exercise or by laughing, coughing, sneezing or the like. The cause of this can be, for example, that the pelvic floor muscle which is a muscle for supporting the urethra is loosened by birth or the like.

For the treatment of urinary incontinence, a surgical treatment is effective, in which there is used, for example, a tape-shaped implant called a "sling." The sling is indwelled inside the body and the urethra is supported by the sling (see, for example, Japanese Patent Laid-Open No. 2010-99499). In order to indwell the sling inside the body, an operator could incise the vagina wall with a surgical knife, dissect a living body tissue between the urethra and the vagina, and, by use of a puncture needle or the like, form a piercing hole which communicates with the dissected living body tissue and the outside of the body. Then, the sling is inserted into the piercing hole, and the sling is indwelled in the dissected living body tissue inside the body.

At the time of inserting the sling into the piercing hole, the inserting operation is conducted with the sling kept inserted in a flexible tube. Since the tube is flexible, however, the tube could be flattened or pressed by the dissected living body tissue. As a result, there have been cases where the friction between the tube and the living body tissue could make it difficult to carry out the sling-inserting operation.

SUMMARY

In accordance with an exemplary embodiment, a medical tube is disclosed, which is configured to have an elongated implant inserted in the medical tube, the medical tube comprising: a tube comprising: a proximal end opening where the tube is open at a proximal end of the tube, and a bent region where an intermediate portion in a longitudinal direction of the tube is bent and where a bent state is maintained; and a connection portion near the proximal end opening and to which a puncture needle having a sharp needle tip at a distal end of the sharp needle is connected from a needle tip side.

In accordance with an exemplary embodiment, a medical tube assembly is disclosed, comprising: a medical tube, the medical tube including a tube, the tube having a proximal end opening where the tube is open at a proximal end of the tube, and a bent region where an intermediate portion in a longitudinal direction of the tube is bent and where a bent state is maintained, and a connection portion near the proximal end opening and to which a puncture needle having a sharp needle tip at a distal end of the sharp needle is connected from a needle tip side; and an elongated implant which is inserted in the medical tube.

In accordance with an exemplary embodiment, a puncture needle is disclosed having a sharp needle tip at a distal end of the puncture needle, the puncture needle comprising: a connection portion which is provided at a distal portion of the puncture needle and to which a proximal portion of a medical tube configured so as to have an elongated implant inserted therein is connected.

BRIEF DESCRIPTION OF THE DRAWINGS

FIGS. 13A and 13B are diagrams as viewed along arrow E in FIG. 4, wherein FIG. 13A shows a state before a separation portion is separated, and FIG. 13B shows a state after the separation portion is separated;

FIG. 14 is a longitudinal sectional view showing a second exemplary embodiment of the medical tube (medical tube assembly) and the puncture needle according to the present disclosure;

DETAILED DESCRIPTION

Figure 1:
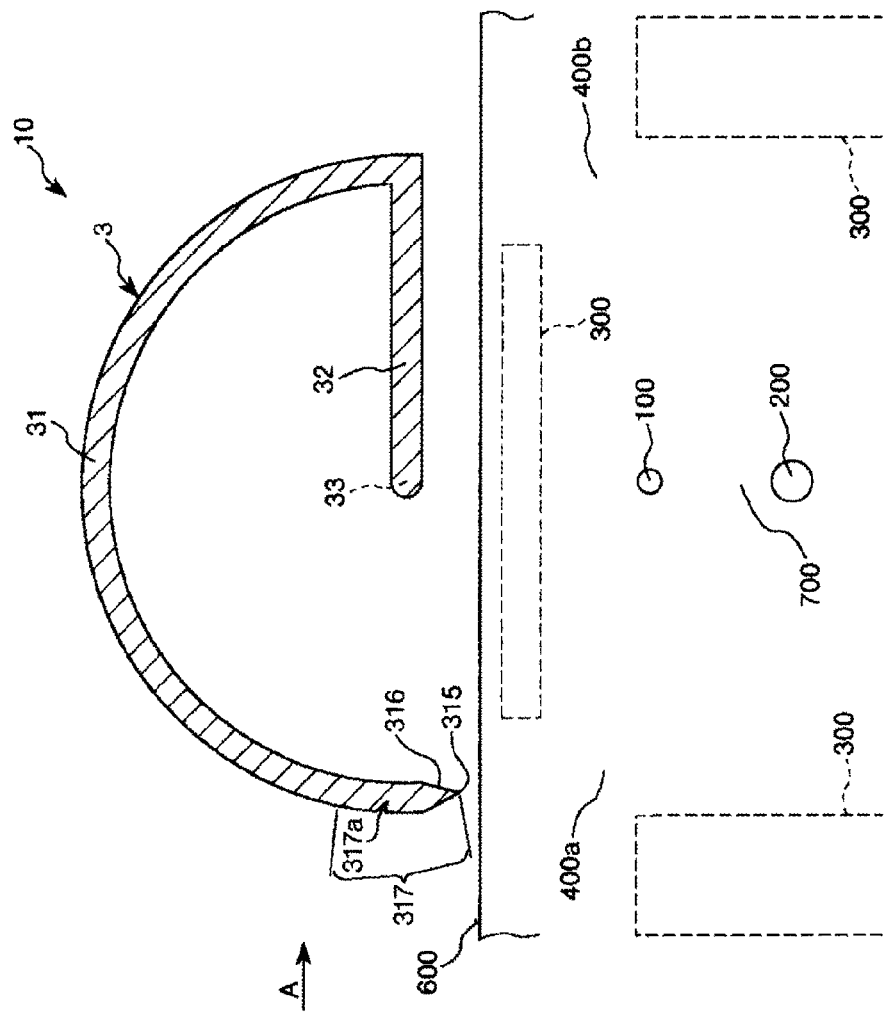
FIG. 1 is a sectional view for sequentially showing a method of use in a first exemplary embodiment of a medical tube (medical tube assembly) and a puncture needle according to the present disclosure.

In accordance with an exemplary embodiment, a medical tube, a medical tube assembly, and a puncture needle are disclosed that can enable a relatively easy and reliable operation at the time of inserting an implant into a living body and indwelling the implant inside the living body.

In accordance with an exemplary embodiment, a medical tube is disclosed, which is configured to have an elongated implant inserted in the medical tube, the medical tube can include a tube which has a proximal end opening where the tube is open at a proximal end of the tube. The tube can include a bent region where an intermediate portion in a longitudinal direction of the tube is bent and where a bent state is maintained. The tube also can include a connection portion which is provided near the proximal end opening and to which a puncture needle having a sharp needle tip at a distal end of the puncture needle is connected from the needle tip side.

In accordance with an exemplary embodiment, the medical tube can be configured such that the tube is rigid at least at the bent region.

In accordance with an exemplary embodiment, the medical tube can be configured such that the connection portion has a small piece formed by forming at least one slit that penetrates the tube wall of the tube, and bending a portion surrounded by the slit toward an inner side.

In accordance with an exemplary embodiment, the medical tube can be configured such that the connection portion has a reduced-diameter part where the tube is reduced in inside diameter.

In accordance with an exemplary embodiment, the medical tube can be configured such that the bent region is bent in an arc shape.

In accordance with an exemplary embodiment, the medical tube can further include a separation portion, which permits the tube to be separated at an intermediate position in the longitudinal direction of the tube.

In accordance with an exemplary embodiment, the medical tube can be configured such that the separation portion is disposed at a central portion in the longitudinal direction of the bent region.

In accordance with an exemplary embodiment, the medical tube can be configured such that the tube is provided with a marker for grasping or identification of the position of the central portion in the longitudinal direction of the bent region.

In accordance with an exemplary embodiment, the medical tube can be configured such that the tube is separated by virtue of the separation portion into a first tube on the distal side and a second tube on the proximal side, and the separation portion is a portion forming a fitting structure in which a proximal portion of the first tube fits in a distal portion of the second tube before the tube is separated into the first tube and the second tube.

In accordance with an exemplary embodiment, the medical tube can be configured such that at least a portion on the distal side as compared with the connection portion is flat in cross-sectional shape.

In accordance with an exemplary embodiment, the medical tube can be configured such that the thickness direction of the flat shape is oriented toward the center of bending of the bent region.

In accordance with an exemplary embodiment, the medical tube can be configured such that the whole length of the tube is longer than the whole length of the puncture needle.

In accordance with an exemplary embodiment, the medical tube can further include a lumen opening into the proximal end opening, and the implant can be inserted in the lumen.

In accordance with an exemplary embodiment, a medical tube assembly is disclosed, which can include the medical tube as disclosed herein and an elongated implant, which can be inserted in the medical tube.

In accordance with an exemplary embodiment, a puncture needle is disclosed having a sharp needle tip at the distal end of the puncture needle, the puncture needle can include a connection portion which is provided at a distal portion of the puncture needle. In accordance with an exemplary embodiment, a proximal portion of a medical tube can be configured to have an elongated implant inserted in the proximal portion of the medical tube, and the proximal portion of the medical tube can be connected to the connection portion.

In accordance with an exemplary embodiment, the puncture needle can be configured such that the connection portion has a cutout where a portion immediately on the proximal side of the needle tip of the puncture needle is partly lost.

In accordance with an exemplary embodiment, the puncture needle can be configured such that the connection portion has a reduced-diameter part where the puncture needle is reduced in outside diameter at a position immediately on the proximal side of the needle tip of the puncture needle.

In accordance with an exemplary embodiment, the bent region can be prevented from being flattened or pressed in the living body when the medical tube is inserted into the living body, which can help ensure that, for example, in the case where an implant is preliminarily inserted in the medical tube, the medical tube can be inserted into the living body together with the implant in a relatively easy and reliable manner.

In accordance with an exemplary embodiment, if only the medical tube is pulled out of the living body after the inserting operation, the implant can be left inside the living body and, hence, placed indwelling inside the living body relatively easily and reliably.

In the state where the medical tube and the puncture needle can be connected to each other by way of the connection portions, the puncture needle can be pulled proximally together with the medical tube, which can help ensure that the medical tube can be relatively easily inserted into and passed through a piercing hole (puncture hole) formed by the puncture needle. In addition, the subsequent indwelling of the implant into the piercing hole (puncture hole) can also be performed relatively easily.

Where the medical tube has the separation portion, the medical tube can be separated (divided) at the separation portion, which can help ensure that the medical tube can be easily pulled out of the living body, and, accordingly, the implant can be indwelled into the living body swiftly.

A medical tube, a medical tube assembly, and a puncture needle according to the present disclosure will now be described in detail, referring to some exemplary embodiments depicted in the accompanying drawings.

Figure 9:
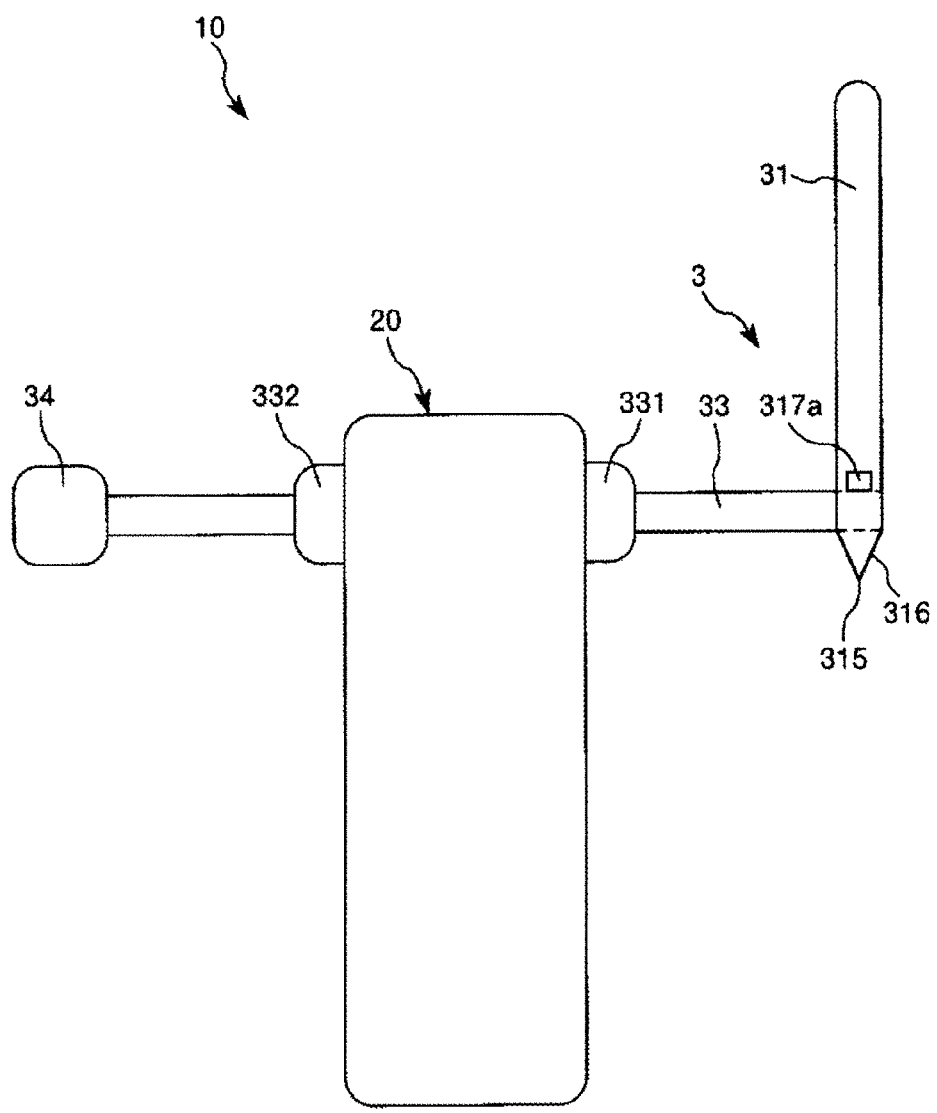
FIG. 9 is a diagram (side view) as viewed along arrow A in FIG. 1.
Figure 10:
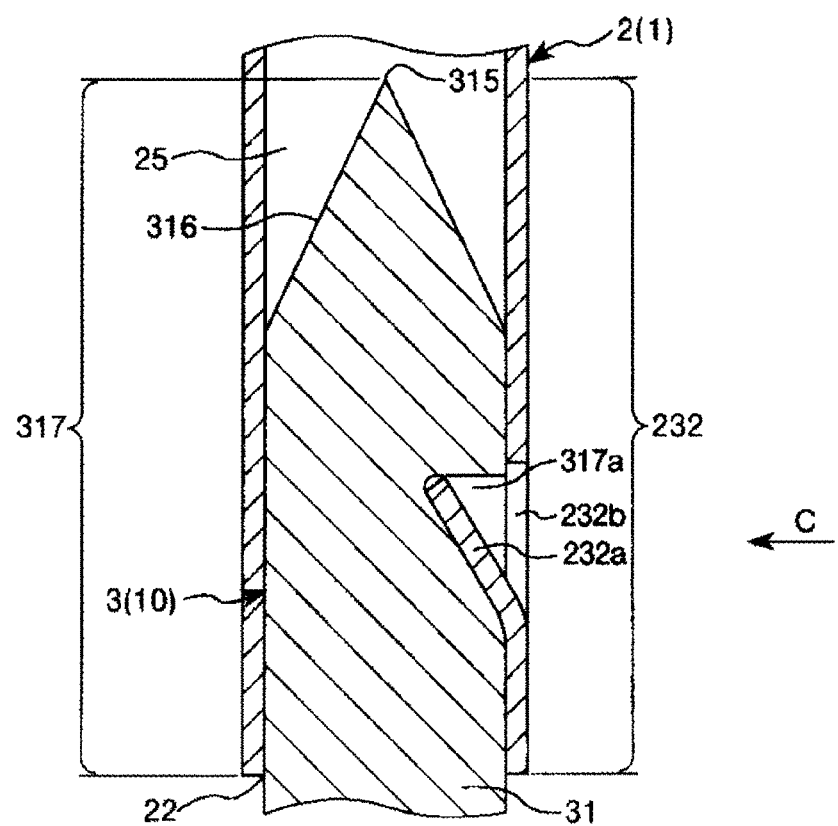
FIG. 10 is an enlarged detailed view of region [B] surrounded by an alternate long and short dash line in FIG. 3.
Figure 11:
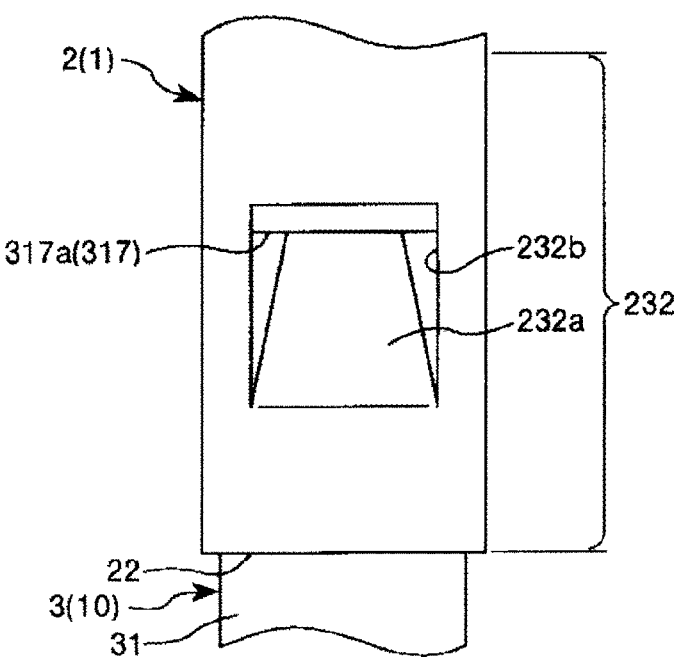
FIG. 11 is a diagram as viewed along arrow C in FIG. 10.
Figure 12:
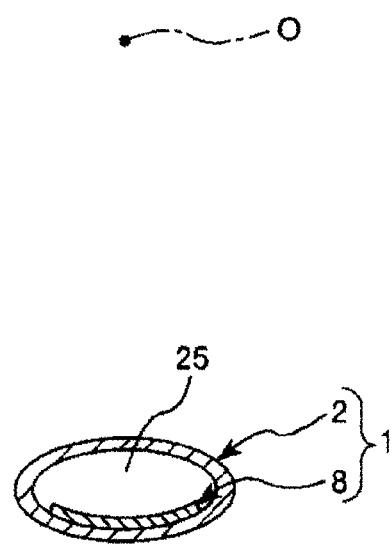
FIG. 12 is a sectional view taken along line 12-12 in FIG. 4.
Figure 13A:
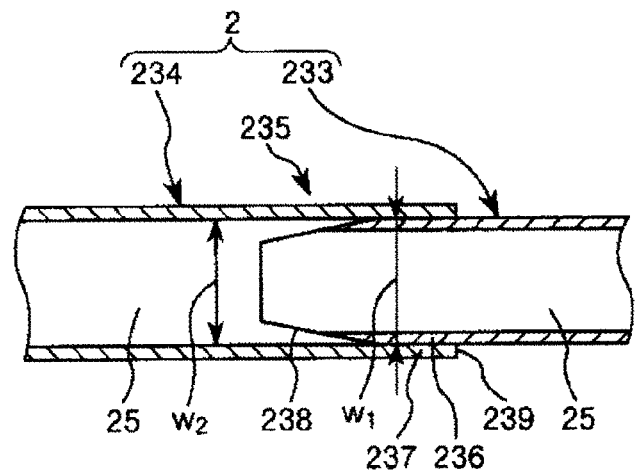
Figure 13B:
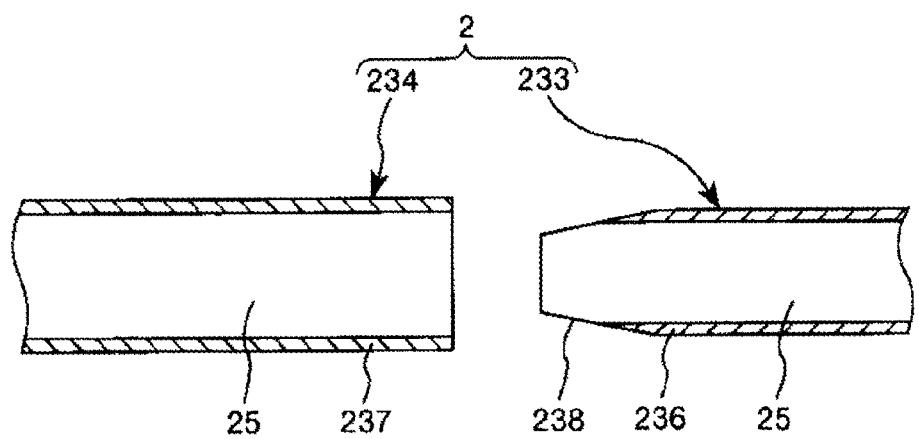

FIGS. 1 to 8 are sectional views for sequentially illustrating a method of use in a first exemplary embodiment of a medical tube (medical tube assembly) and a puncture needle according to the present disclosure; FIG. 9 is a diagram (side view) as viewed along arrow A in FIG. 1; FIG. 10 is an enlarged detailed view of region [B] surrounded by an alternate long and short dash line in FIG. 3; FIG. 11 is a diagram as viewed along arrow C in FIG. 10; FIG. 12 is a sectional view taken along line 12-12 in FIG. 4; and FIGS. 13A and 13B can be diagrams as viewed along arrow E in FIG. 4, wherein FIG. 13A shows a state before a separation portion is separated, and FIG. 13B shows a state after the separation portion is separated. Note that in the following description, the upper side in FIGS. 1 to 9 (and in FIGS. 15 to 17, as well) will be referred to as "upper" or the "upper side," and the lower side in the figures as "lower" or the "lower side," for convenience of description. In addition, the side of a needle tip will be referred to as the "distal side," and the opposite side as the "proximal side."

Figure 3:
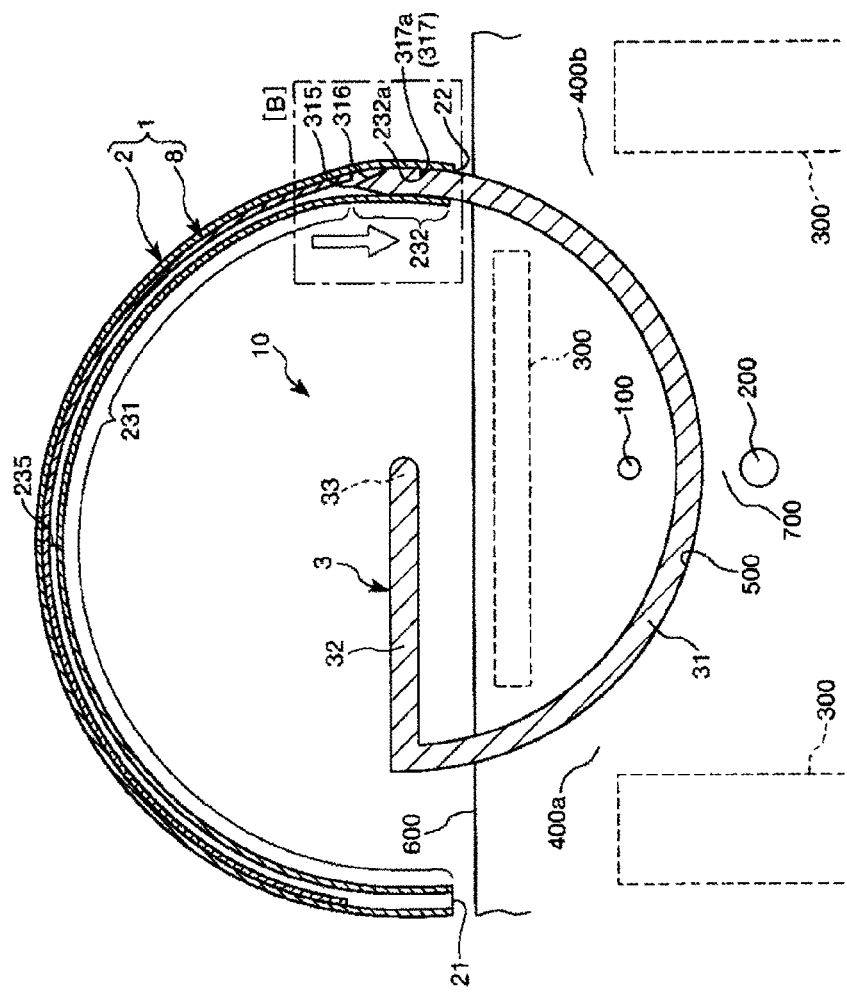
FIG. 3 is a sectional view for sequentially showing the method of use in the first exemplary embodiment of the medical tube (medical tube assembly) and the puncture needle.
Figure 4:
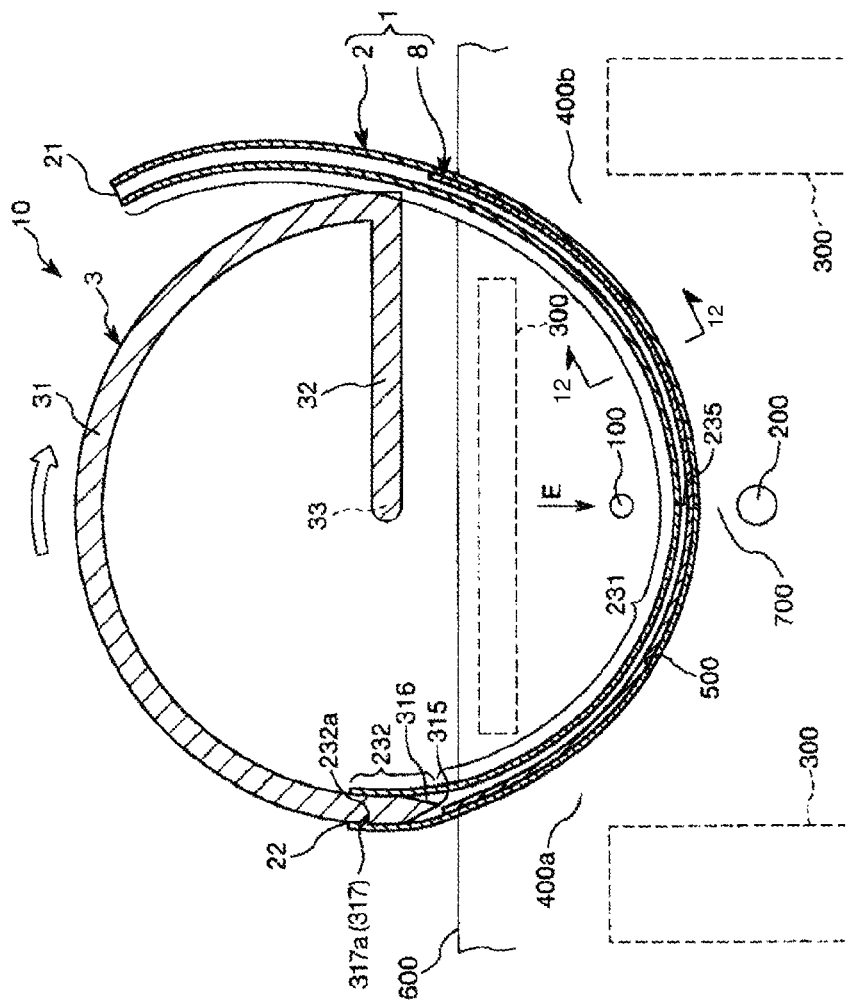
FIG. 4 is a sectional view for sequentially showing the method of use in the first exemplary embodiment of the medical tube (medical tube assembly) and the puncture needle.
Figure 5:
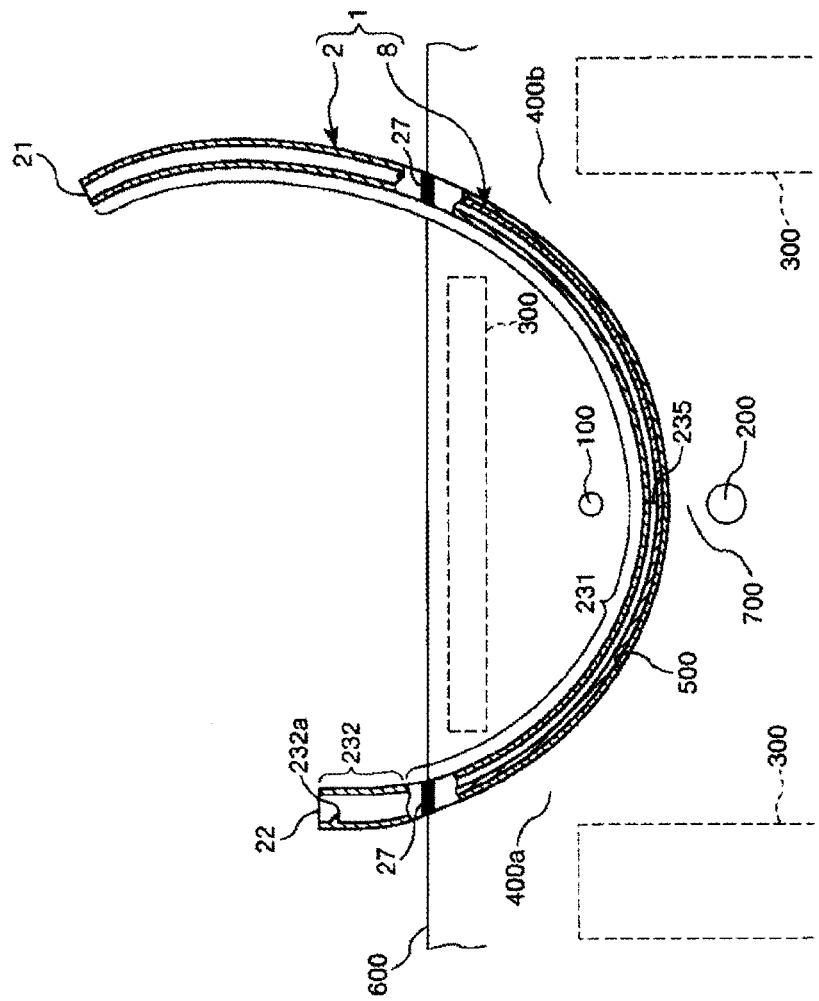
FIG. 5 is a sectional view for sequentially showing the method of use in the first exemplary embodiment of the medical tube (medical tube assembly) and the puncture needle.
Figure 6:
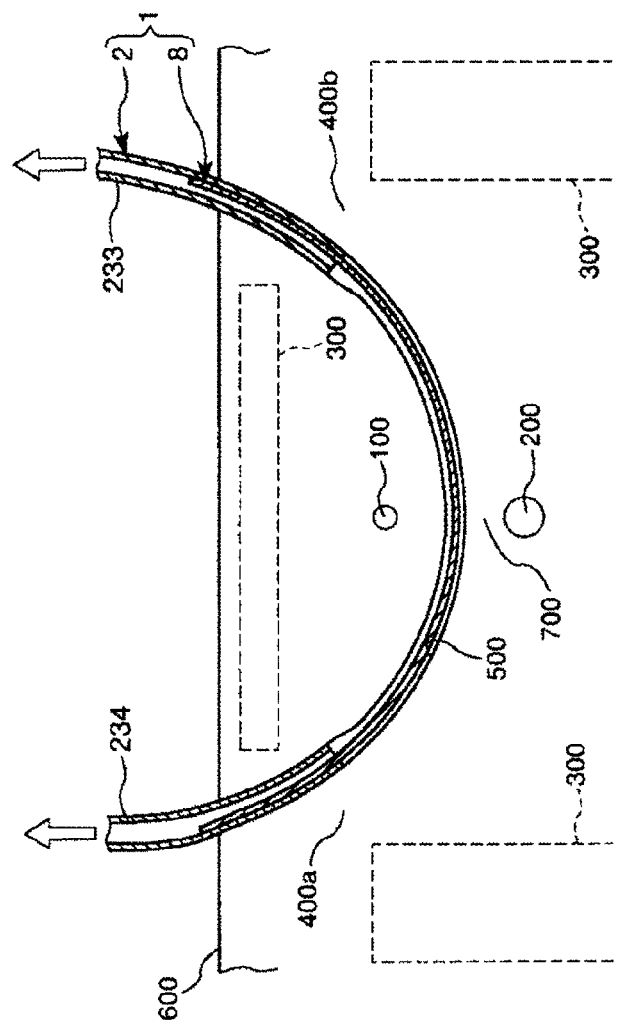
FIG. 6 is a sectional view for sequentially showing the method of use in the first exemplary embodiment of the medical tube (medical tube assembly) and the puncture needle.

In accordance with an exemplary embodiment, a medical tube assembly 1 shown in FIGS. 4 to 6 can include a medical tube (tube) 2, and an implant 8 which is inserted in the medical tube 2. The medical tube assembly 1 can be a medical device used in treatment of female urinary incontinence. In accordance with an exemplary embodiment, when treatment of female urinary incontinence is performed, a puncture apparatus 10 can also be used together with the medical tube assembly 1, as shown in FIGS. 1 to 4. In this embodiment, the medical tube assembly 1 and the puncture apparatus 10 together constitute a "medical device set" for treatment of female urinary incontinence. The configuration of each of the components will now be described below.

First, the implant 8 will be described. The implant 8 is a device which, is commonly called a "sling", which can be an implantable device for treatment of female urinary incontinence, for example, for supporting a urethra 100 in the manner of, for example, pulling the urethra 100 in a direction for spacing away (or spaced apart) from a vagina 200 when the urethra 100 could otherwise be going to move toward the vagina 200 side (see FIG. 8). The implant 8 can include a band-like (elongated) member, which can be flexible (see FIGS. 3 to 8).

The constituent material of the implant 8 is not specifically restricted. Examples of the material applicable here, can include, for example, various resin materials that can be biocompatible.

In accordance with an exemplary embodiment, the implant 8 can be preliminarily inserted (stored or housed) in the medical tube 2 as depicted in FIG. 3, or can be inserted into the medical tube 2 in the course of a procedure. Where the implant 8 is preliminarily inserted in the medical tube 2, a procedure can be relatively swiftly performed. Where the implant 8 is inserted into the medical tube 2 in the course of a procedure, an implant 8 suited to an individual case can be selected in each procedure according to the case. In this embodiment, a case where the implant 8 is preliminarily inserted in the medical tube 2 will be described on a representative basis.

Now, the puncture apparatus 10 will be described, prior to a description of the medical tube 2.

As shown in FIGS. 1 to 4 and 9, the puncture apparatus 10 can include a puncture member 3, and a support member 20 which supports the puncture member 3 so that the puncture member 3 is rotatable. In accordance with an exemplary embodiment, the puncture apparatus 10 can include a bar-shaped urethral-insertion member to be inserted in the urethra 100, and a bar-shaped vaginal-insertion member to be inserted into the vagina 200. In accordance with an exemplary embodiment, these members can be individually supported on and fixed to the support member 20.

The puncture member 3 can include a puncture needle 31 configured to puncture a living body tissue 700, an axial portion 33, and an interlock portion 32 interlocking the puncture needle 31 and the axial portion 33 to each other.

The puncture needle 31 has a sharp needle tip 315 at a distal end of the puncture needle 31, and can be bent in an arc shape centered on the axial portion 33. In addition, the axis of the puncture needle 31 and the axis of the axial portion 33 can be in the relationship of skew lines, which can help ensure that when the puncture member 3 is rotationally moved about the axial portion 33, the needle tip 315 of the puncture needle 31 is moved along the arc, in a plane orthogonal to the axis of the axial portion 33, namely, in a plane to which the axis of the axial portion 33 is a normal.

In accordance with an exemplary embodiment, a center angle of the arc of the puncture needle 31 is not particularly limited, and can be appropriately set according to various conditions, in such a manner that when the living body tissue 700 is punctured by the puncture needle 31, a piercing hole (puncture hole) 500 in an arc shape is formed in the living body tissue 700 as will be described later. Such a center angle, for example, can be about 120 to 270 degrees, more preferably about 160 to 230 degrees, and further preferably about 180 to 210 degrees.

While the needle tip 315 of the puncture needle 31 is oriented counterclockwise in FIGS. 1 to 4 in this embodiment, this is not restrictive, and the needle tip 315 can be oriented clockwise in the figures.

The puncture needle 31 can be formed with a tapered portion 316 where the outside diameter of the puncture needle 31 gradually increases along the proximal direction from the needle tip 315.

In addition, the puncture needle 31 can be a solid needle or can be a hollow needle.

The axial portion 33 constitutes a rotation axis for the puncture member 3 (puncture needle 31), and is disposed so as to be rotatable on the support member 20.

As shown in FIG. 9, the axial portion 33 penetrates the support member 20 along the left-right direction in the figure. A flange 331 and a flange 332 can be formed respectively at a distal-side portion and a proximal side portion of the axial portion 33, with the support member 20 interposed between the flanges 331, 332. In accordance with an exemplary embodiment, the flanges 331 and 332 can restrict axial movement of the axial portion 33 relative to the support member 20.

In addition, the axial portion 33 can be provided, at an end portion on the side opposite to the puncture needle 31, with a grasping portion 34 as an operating portion for a rotary movement operation of the puncture member 3. In accordance with an exemplary embodiment, the shape of the grasping portion 34 is a rectangular parallelepiped shape. At the time of putting the puncture member 3 into a rotary movement, the grasping portion 34 can be grasped with fingers and rotated in a predetermined direction. Note that the shape of the grasping portion 34 is naturally not restricted to the just-mentioned.

The interlock portion 32 is a portion which interlocks the proximal end of the puncture needle 31 and the axial portion 33.

The constituent material of the puncture member 3 is not specifically restricted. Examples of the material usable here, for example, can include various metallic materials such as stainless steel, aluminum or aluminum alloys, titanium or titanium alloys, etc.

The support member 20 is a member, which can support the puncture member 3 so that the puncture member 3 is rotatable. Note that the support member 20 is omitted in FIGS. 1 to 4.

The support member 20 can restrict the position of the puncture member 30 so that when the puncture member 3 rotates and punctures the living body tissue 700, the needle tip 315 of the puncture needle 31 passes between the urethra 100 and the vagina 200. In accordance with an exemplary embodiment, the puncture needle 31 forms the arc-shaped piercing hole 500 between the urethra 100 and the vagina 200.

The constituent material of the support member 20 is not specifically restricted. For example, various resin materials such as polyethylene and polypropylene can be used.

Now, the medical tube 2 will be described below. As depicted in FIGS. 3 to 5, the medical tube 2 is a tube having a distal end opening 21 where the distal end of the tube is open, and a proximal end opening 22 where the proximal end of the tube is open.

In addition, the medical tube 2 can be formed with a lumen 25 opening into the distal end opening 21 and the proximal end opening 22. The implant 8 can be inserted in the lumen 25. Note that while only one lumen is formed in this exemplary embodiment, the number of the lumen(s) is not limited to one, and can be, for example, two or more.

As shown in FIGS. 3 to 5, the medical tube 2 can have a bent region 231 where an intermediate portion in the longitudinal direction of medical tube 2 is bent in an arc shape. The medical tube 2 can be rigid at least at the bent region 231. In accordance with an exemplary embodiment, the term "rigid" used here means an extent of rigidity such that the bent region 231 can maintain its arc-shaped bent state by itself. In addition, the degree of bending (curvature) of the bent region 231 can be comparable to or lower than that of the puncture needle 31 of the puncture apparatus 10.

The just-mentioned configuration can help ensure that when the medical tube 2 is inserted into the piercing hole 500 formed by the puncture apparatus 10, the bent region 231 is prevented from being flattened or pressed inside the piercing hole 500, and the bent region 231 can easily follow the bent shape of the piercing hole 500. Consequently, an operation of inserting the medical tube 2 into the piercing hole 500 (living body) together with the implant 8 can be carried out relatively easily and reliably. In addition, with the medical tube 2 separated (as will be described later) after the inserting operation, the implant 8 can be indwelled in the piercing hole 500 easily and assuredly (see FIG. 6).

As illustrated in FIG. 12, the cross-sectional shape of the bent region 231, or the cross-sectional shape of that portion of the medical tube 2 which is on the more distal side than the vicinity of the proximal end opening 22 (connection portion 232), is a somewhat flat shape, specifically, an elliptic shape. This cross-sectional shape ensures that in the case where the band-shaped implant 8 is preliminarily inserted in the lumen 25, the inserting operation can be carried out easily. It also ensures that it is possible to form a space for reliable insertion of the implant 8 in the piercing hole 500. It further ensures that the orientation of the implant 8 can be restricted.

Note that the cross-sectional shape of the bent region 231 can be other shape than the somewhat flat shape, for example, a circular shape.

As shown in FIG. 12, the thickness direction (minor-diameter direction) of the relatively flat shape can be oriented toward the center of bending (curvature) O of the bent region 231. This configuration can contribute to a relatively easy insertion of the medical tube 2 into the piercing hole 500, as compared with the case where the width direction (major-diameter direction) of the relatively flat shape is oriented toward the center of bending (curvature) O.

As depicted in FIGS. 3 and 4, the medical tube 2 is provided, in the vicinity of the proximal end opening 22, with the connection portion (tube-side connection portion) 232 into which the puncture needle 31 of the puncture member 3 is to be inserted and connected from the needle tip 315 side. In accordance with an exemplary embodiment, the puncture needle 31 is provided at its distal end portion with a connection portion (puncture needle side connection portion) 317 to which the connection portion 232 (proximal end portion) of the medical tube 2 is to be connected.

As shown in FIGS. 10 and 11, the connection portion 232 of the medical tube 2 has a small piece 232a at a portion on an outer side with respect to the bend. The small piece 232a can be configured by forming a roughly U-shaped slit 232b that penetrates the tube wall of the medical tube 2, and bending the portion surrounded by the slit 232b toward the inner side. In FIG. 11, the slit 232b is an inverted U-shaped, and wherein the U-shape is opening toward the proximal side (toward the lower side in FIG. 11).

In addition, the connection portion 317 of the puncture needle 31 can have a cutout 317a where the connection portion 317 is partly lost. The cutout 317a can be located immediately on the proximal side of, and on the outer side with respect to the bend of, the needle tip 315. The cutout 317a is formed in a wedge-like shape such that the depth of the cutout 317a gradually decreases along the proximal direction (along the downward direction in FIG. 10).

As illustrated in FIGS. 10 and 11, in a state where the connection portion 232 of the medical tube 2 and the connection portion 317 of the puncture needle 31 can be connected to each other (this state will hereinafter be referred to as the "connected state"), the small piece 232a of the connection portion 232 can engage the cutout 317a of the connection portion 317, which can help ensures that the connected state is reliably maintained, and an unintended canceling of the connected state can help be prevented.

As shown in FIGS. 3 and 4, by rotating the puncture member 3 clockwise in the figures in the connected state, the medical tube 2 can be pulled in that direction. By this operation, the medical tube 2 can be relatively easily inserted into and passed through the piercing hole 500, and the subsequent indwelling of the implant 8 into the piercing hole 500 can be relatively easily performed.

In accordance with an exemplary embodiment, the connection portion 232 can be rigid like the bent region 231, or can be soft or flexible.

As illustrated in FIGS. 6 and 13B, the medical tube 2 can be configured that it can be separated (divided), at an intermediate portion in the longitudinal direction thereof, into a first tube 233 on the distal side and a second tube 234 on the proximal side. This separation (division) makes it possible to swiftly withdraw the medical tube 2 out of the piercing hole 500, and leaving only the implant 8 indwelling in the piercing hole 500.

As shown in FIGS. 3 to 5, a separation portion 235 for this separation (division) is located at a central portion in the longitudinal direction of the bent region 231, which can help enable the urethra 100 to be suitably supported by the implant 8 upon separation (division) of the medical tube 2 at the separation portion 235, as depicted in FIG. 6.

In accordance with an exemplary embodiment, preferably, markers 27 for grasping the central portion in the longitudinal direction of the bent region 231 can be provided respectively at a distal portion and a proximal portion of the medical tube 2 (see FIG. 5). The markers 27 can help enable reliable grasping of the position of the central portion in the longitudinal direction of the bent region 231, namely, the position of the separation portion 235. Note that while the markers 27 can be provided respectively at both the distal portion and the proximal portion of the medical tube 2 in this exemplary embodiment, this configuration is not restrictive, and, for example, a marker can only be provided at one of the distal portion and the proximal portion of the medical tube 2.

As depicted in FIG. 13A, before the separation (division) of the medical tube 2 into the first tube 233 and the second tube 234, the separation portion 235 constitutes a fitting structure in which a proximal end portion 236 of the first tube 233 fits inside a distal end portion 237 of the second tube 234, which can help ensure that when the medical tube 2 is pulled from both sides of the medical tube 2, the fitting state between the proximal end portion 236 of the first tube 233 and the distal end portion 237 of the second tube 234 can be canceled in a relatively assured manner. By this canceling of the fit, the medical tube 2 can be relatively easily separated at the separation portion 235 into the first tube 233 and the second tube 234.

Note that the proximal end portion 236 of the first tube 233 can be formed with a gradually decreasing width portion 238 where the width of the proximal end portion 236 gradually decreases along proximally, which can help ensure that when the medical tube 2 is to be left in the state as depicted in FIG. 13A, the proximal end portion 236 of the first tube 233 can be relatively easily inserted into the distal end portion 237 of the second tube 234, resulting in the fitting state between the end portions.

In addition, the outside width (maximum width) $w_1$ of the proximal end portion 236 of the first tube 233 can be equal to or slightly smaller than the inside width $w_2$ of the distal end portion 237 of the second tube 234, which can help permit easier insertion of the proximal end portion 236 of the first tube 233 into the distal end portion 237 of the second tube 234.

As disclosed, the fitting structure between the proximal end portion 236 of the first tube 233 and the distal end portion 237 of the second tube 234 is such that the proximal end portion 236 is located on the inner side and the distal end portion 237 is located on the outer side. In this case, for example, at the separation portion 235, specifically, in the boundary area between the proximal end portion 236 and the distal end portion 237, there is formed a step 239 where the width of the medical tube 2 is reduced stepwise along the distal direction (see FIG. 13A). Since the medical tube 2 can be inserted into the piercing hole 500, starting from the proximal end of the medical tube, it can be preferable that the step 239 is formed in the just-mentioned fashion.

In accordance with an exemplary embodiment, the length of the medical tube 2 is preferably longer than the length of the puncture needle 31. Accordingly, the medical tube 2 is longer than the length of the piercing hole 500 formed by the puncture needle 31, so that both end portions of the medical tube 2 protrude from the piercing hole 500 in a state where the medical tube 2 is inserted in and passed through the piercing hole 500 as illustrated in FIGS. 4 and 5. When separating the medical tube 2 into the first tube 233 on the distal side and the second tube 234 on the proximal side and pulling these tubes out of the piercing hole 500, the pulling-out operation can be performed by grasping the protruding end portions.

The constituent material of the medical tube 2 is not specifically restricted. Examples of the material applicable here, for example, can include polyolefins such as polyethylene, polypropylene, ethylene-vinyl acetate copolymer, modified polyolefins, polyamides (for example, nylon 6, nylon 46, nylon 66, nylon 610, nylon 612, nylon 11, nylon 12, nylon 6-12, and nylon 6-66), thermoplastic polyimides, liquid crystal polymers such as aromatic polyesters, polyphenylene oxide, polyphenylene sulfide, polycarbonate, polymethyl methacrylate, polyethers, polyether-ether ketone, polyether-imides, polyacetal, various thermoplastic elastomers based on styrene, polyolefin, polyvinyl chloride, polyurethane, polyester, polyamide, polybutadiene, trans-polyisoprene, fluoro-rubber, chlorinated polyethylene or the like, and copolymers, polymer blends, polymer alloys, etc. containing the just-mentioned polymers. These materials can be used either singly or as a mixture of two or more of them.

Now, an exemplary method of using the medical tube assembly 1 and the puncture apparatus 10 will be described below, referring to FIGS. 1 to 8.

[1] First, as shown in FIG. 1, the puncture apparatus 10 can be mounted onto a patient's body surface 600. The mounting position in this instance can be a position suitable for supporting the urethra 100 by the implant 8 that is going to be implanted.

Figure 2:
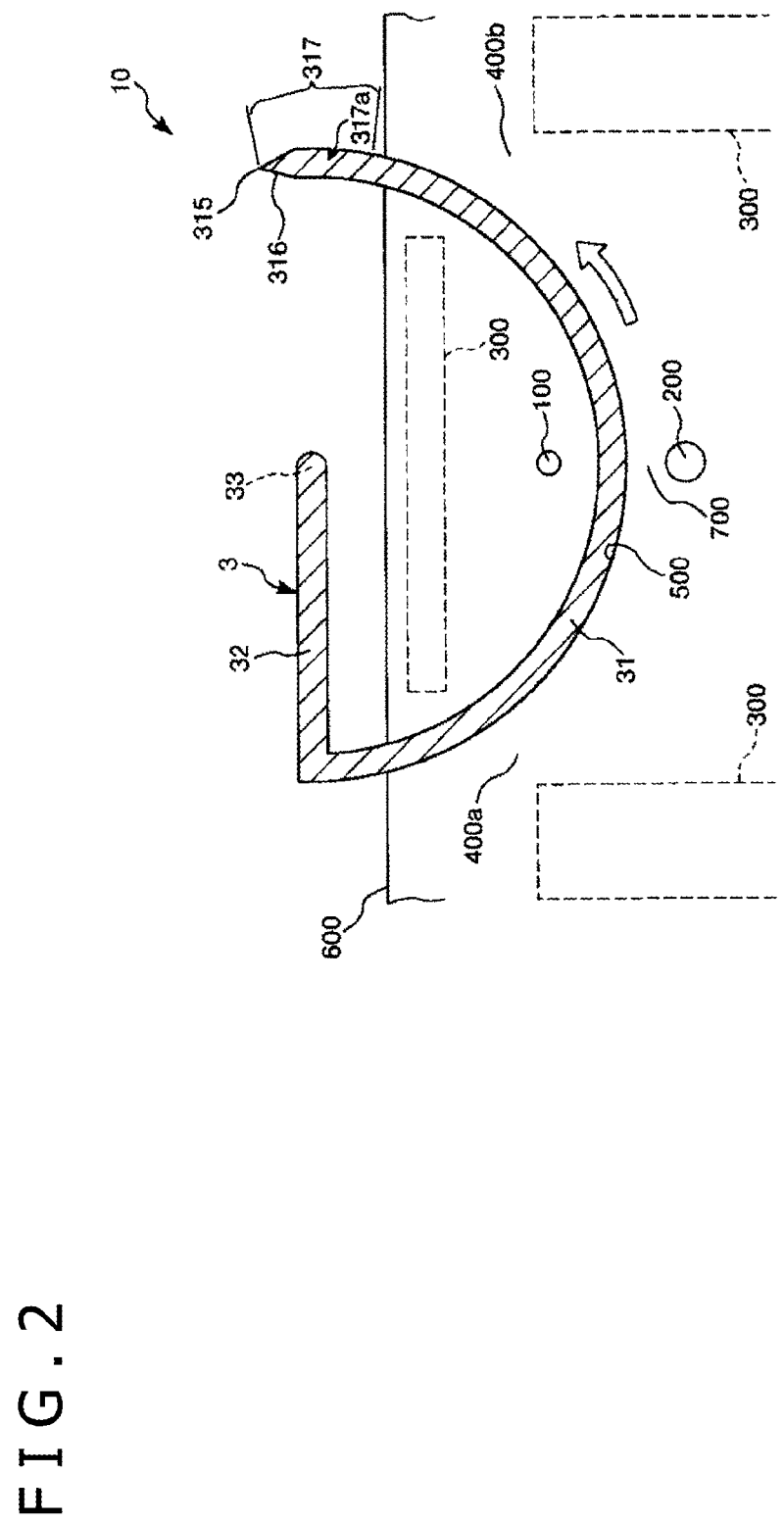
FIG. 2 is a sectional view for sequentially showing the method of use in the first exemplary embodiment of the medical tube (medical tube assembly) and the puncture needle.

[2] Next, with the grasping portion 34 of the puncture apparatus 10 grasped by one hand, the puncture member 3 is rotated counterclockwise as shown in FIG. 2. Upon this rotation, the puncture needle 31 is moved with the axial portion 33 as a rotation center, to sequentially pass (puncture) an inguinal region on the left side in the figure (or a region in the vicinity of the inguinal region) of the patient's body surface 600, an obturator foramen 400a in a pelvis 300, a region between the urethra 100 and the vagina 200, an obturator foramen 400b in the pelvis 300, and an inguinal region on the right side in the figure (or a region in the vicinity of the inguinal region) of the body surface 600. As a result of the puncturing, the piercing hole 500 that penetrates the living body tissue 700 from the left-side inguinal region of the body surface 600 to the right-side inguinal region of the body surface 600 is formed in the living body tissue 700. In accordance with an exemplary embodiment, the puncture needle 31 has its connection portion 317 protruding from the right-side inguinal region of the body surface 600.

[3] Subsequently, the medical tube assembly 1 with the implant 8 inserted in the medical tube 2 is prepared. As shown in FIG. 3, the connection portion 317 of the puncture needle 31 is inserted into the connection portion 232 of the medical tube 2, and the connection portions 317 and 232 can be connected to each other. As a result, the medical tube 2 and the puncture needle 31 can be in a connected state. In this connected state, the small piece 232a of the connection portion 232 is in engagement with the cutout 317a in the connection portion 317, as disclosed. By the engagement, the connected state can be maintained reliably.

[4] Next, with the grasping portion 34 of the puncture apparatus 10 grasped by one hand, the puncture member 3 is rotated in the direction opposite to the above-mentioned, namely, rotated clockwise in FIG. 4, as shown in the figure. Upon this rotation, the puncture member 3 is pulled out of the piercing hole 500, and, this time, the medical tube assembly 1 (medical tube 2) is inserted into and passed through the piercing hole 500. The medical tube assembly 1 is now in a state in which its distal-side portion is protruding from the body surface 600 on the side of the obturator foramen 400b, whereas its proximal-side portion is protruding from the body surface 600 on the side of the obturator foramen 400a.

[5] Subsequently, as shown in FIG. 5, the puncture member 3 of the puncture apparatus 10 is taken away (or removed) from the body surface 600 together with the support member 20.

[6] Next, of the medical tube assembly 1, the portion protruding from the body surface 600 on the side of the obturator foramen 400b is grasped by one hand, while the portion protruding from the body surface 600 on the side of the obturator foramen 400a is grasped by the other hand, and the grasped portions can be pulled in opposite directions, as illustrated in FIG. 6. As a result, the medical tube 2 is separated (divided) into the first tube 233 and the second tube 234 by virtue of the separation portion 235.

Figure 7:
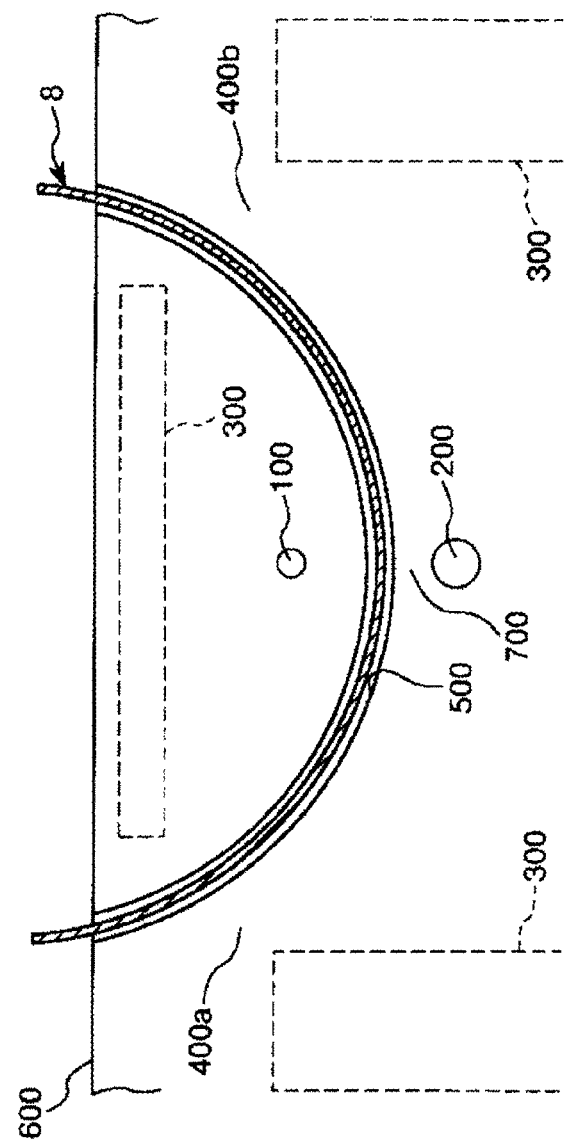
FIG. 7 is a sectional view for sequentially showing the method of use in the first exemplary embodiment of the medical tube (medical tube assembly) and the puncture needle.

[7] Subsequently, the first tube 233 and the second tube 234 can be individually pulled out of the piercing hole 500, whereon the implant 8 is left inserted in and passed through the piercing hole 500, as shown in FIG. 7. The implant 8 is now in a state in which its distal-side portion is protruding from the body surface 600 on the side of the obturator foramen 400b, whereas its proximal-side portion is protruding from the body surface 600 on the side of the obturator foramen 400a. Then, the distal-side portion and the proximal-side portion of the implant 8 can be pulled with respective predetermined forces. As a result, a tension is generated on the implant 8, whereby the urethra 100 is pulled in a direction for spacing away from the vagina 200 and is supported by the implant 8 from below.

Figure 8:
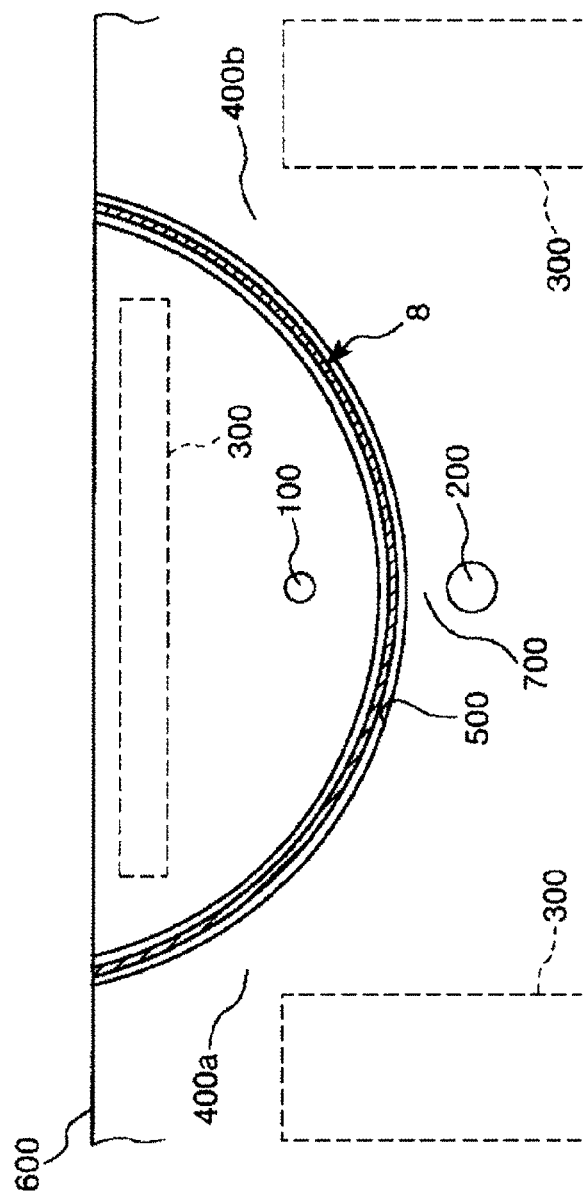
FIG. 8 is a sectional view for sequentially showing the method of use in the first exemplary embodiment of the medical tube (medical tube assembly) and the puncture needle.

[8] Next, as shown in FIG. 8, unnecessary portions of the implant 8 can be cut away, and predetermined wound closure and the like can be conducted, to finish the procedure.

In the above-disclosed procedure, or treatment of urinary incontinence, at the time of inserting the implant 8 into the piercing hole 500 and indwelling the implant 8 in situ, the implant 8 has preliminarily been housed in the medical tube 2 and is inserted into the piercing hole 500 together with the medical tube 2. The medical tube 2 is rigid, at least at its bent region 231, as disclosed. Therefore, the medical tube 2 can be prevented from unintentionally being deformed through being flattened or pressed by the living body tissue 700 when situated in the piercing hole 500. Accordingly, the operation of inserting the implant 8 (together with the medical tube 2) into the piercing hole 500 can be carried out relatively easily and reliably.

In addition, in the present procedure, the medical tube 2 can be relatively easily pulled out of the piercing hole 500 through the separation of the medical tube 2, after the implant 8 is inserted into the piercing hole 500 together with the medical tube 2. Consequently, the implant 8 is indwelled in the piercing hole 500 in a reliable manner.

In accordance with an exemplary embodiment, in the connected state, the puncture needle 31 can be pulled proximally together with the medical tube 2. This ensures that the medical tube 2 can easily be inserted into and passed through the piercing hole 500, and the subsequent indwelling of the implant 8 into the piercing hole 500 can also be carried out relatively easily.

FIG. 14 is a longitudinal sectional view showing a second exemplary embodiment of the medical tube (medical tube assembly) and the puncture needle according to the present disclosure.

Referring to this figure, the second embodiment of the medical tube, the medical tube assembly and the puncture needle according to the present disclosure will be described below. In the following, description will be mainly made of differences of the second embodiment from the first exemplary embodiment, and the same or similar items to those described above will be omitted from the description.

In accordance with an exemplary embodiment, the second exemplary embodiment is the same as the first embodiment above, except for differences in the configurations of connection portions of the medical tube and the puncture needle.

As depicted in FIG. 14, in this embodiment, a connection portion 232 of a medical tube 2A has a reduced-diameter part 232c where the medical tube 2A is reduced in inside diameter. The reduced-diameter part 232c can be formed, for example, by heat shrinkage of that portion of the medical tube 2A which is to be the reduced-diameter part 232c.

In addition, a connection portion 317 of a puncture needle 31 of a puncture member 3A has a reduced-diameter part 317b where the puncture needle 31 is reduced in outside diameter at a position immediately on the proximal side of a tapered portion 316 of a needle tip 315. The reduced-diameter part 317b can be formed, for example, by cutting that portion of the puncture needle 31, which is to be the reduced-diameter part 317b.

In a connected state, the reduced-diameter part 232c of the connection portion 232 of the medical tube 2A is in engagement with the reduced-diameter part 317b of the connection portion 317 of the puncture needle 31. By this engagement, the connected state can be securely maintained. Consequently, the medical tube 2A can be made to pass a piercing hole 500, following the puncture member 3A, as previously disclosed.

Figure 15:
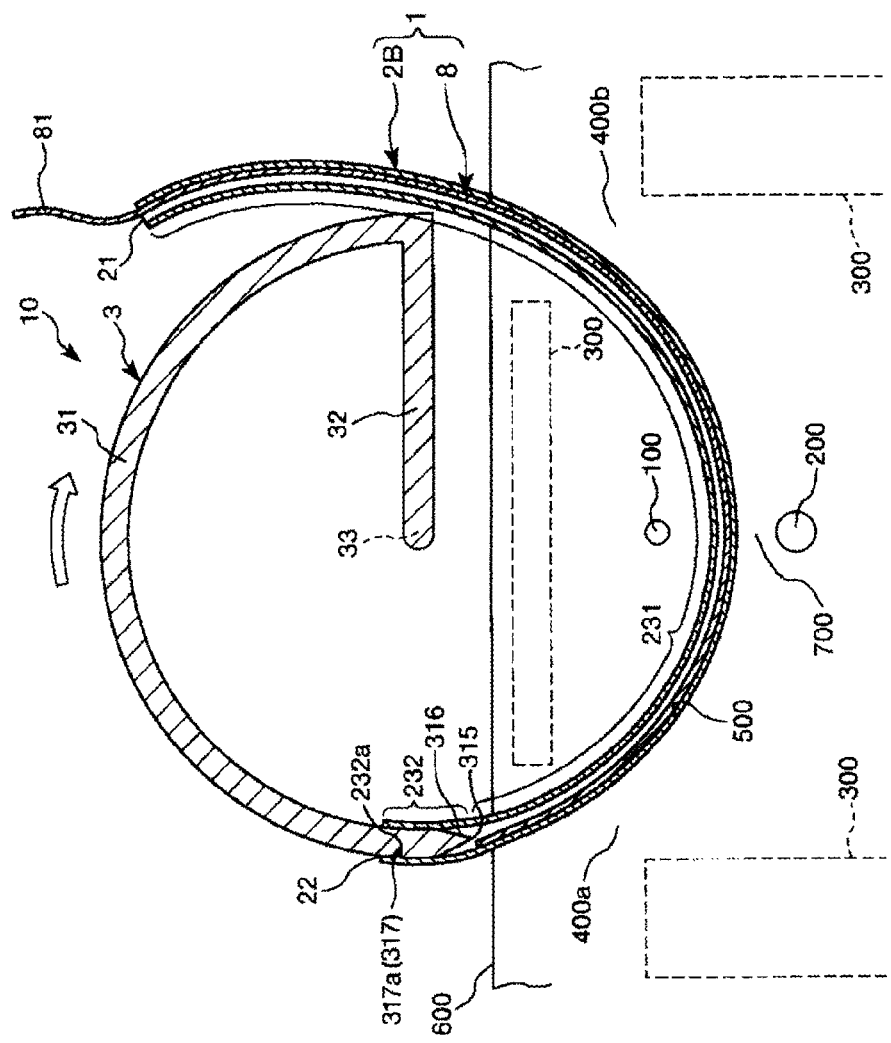
FIG. 15 is a sectional view for sequentially showing a method of use in a third exemplary embodiment of the medical tube (medical tube assembly) according to the present disclosure.
Figure 16:
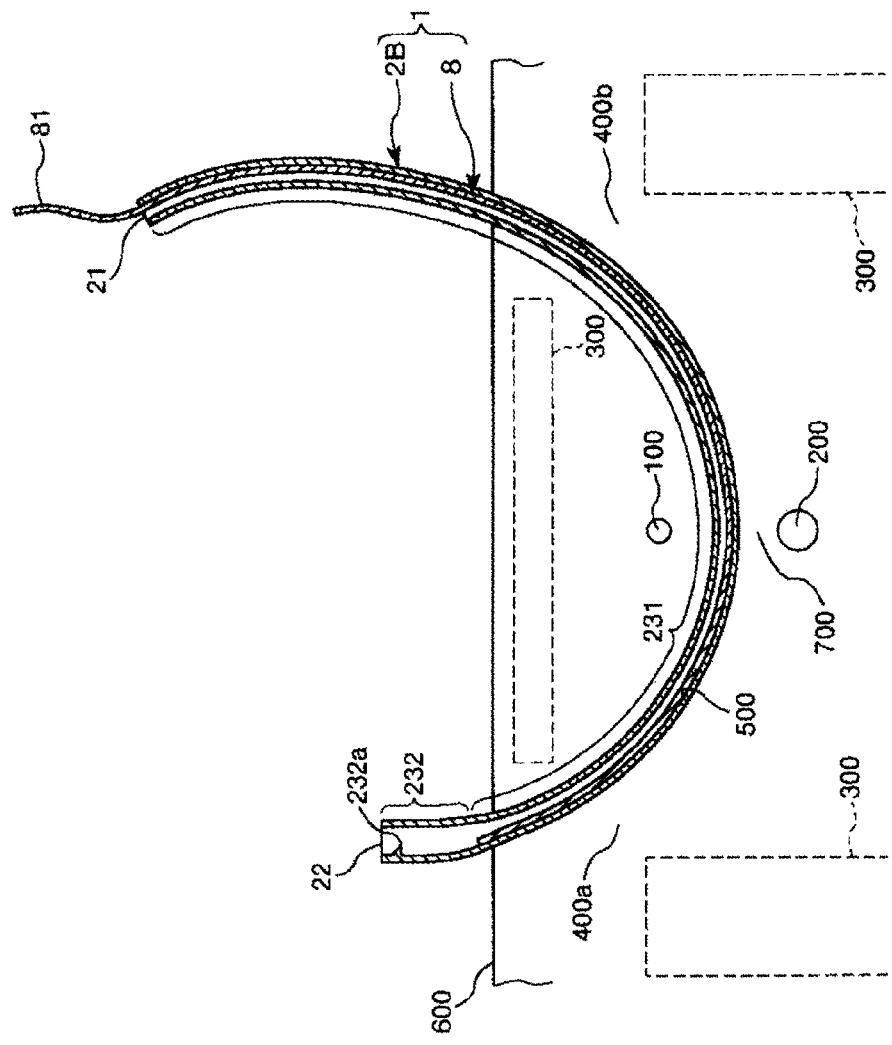
FIG. 16 is a sectional view for sequentially showing the method of use in the third exemplary embodiment of the medical tube (medical tube assembly)
Figure 17:
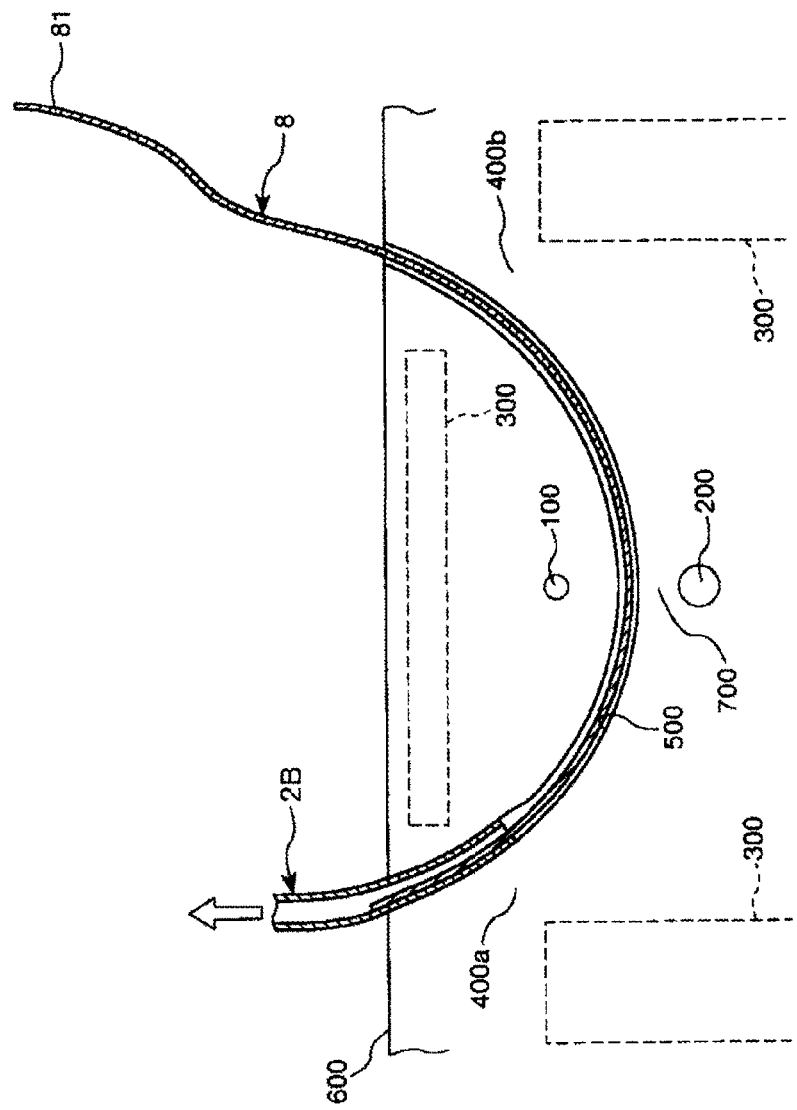
FIG. 17 is a sectional view for sequentially showing the using method in the third exemplary embodiment of the medical tube (medical tube assembly).

FIGS. 15 to 17 are sectional views for sequentially illustrating a method for use in a third exemplary embodiment of the medical tube (medical tube assembly) according to the present disclosure.

The third exemplary embodiment of the medical tube, medical tube assembly and puncture needle according to the present disclosure will be described below, referring to these figures. In the following, description will be mainly made of differences of the third embodiment from the above embodiments, and the same or similar items to those described above will be omitted from the description.

The third exemplary embodiment is the same as the first embodiment above, except that the separation portion is omitted from the medical tube.

As shown in FIGS. 15 and 16, a medical tube 2B in this embodiment can have a configuration wherein a separation portion, such as the separation portion 235 possessed by the medical tube 2 in the first embodiment above, is omitted.

In accordance with an exemplary embodiment, a distal portion 81 of an implant 8 can be preliminarily set protruding from a distal end opening 21 of the medical tube 2B.

An exemplary method of using a medical tube assembly 1 possessing the medical tube 2B configured as above will be described, referring to FIGS. 15 to 17. Note that this using method is the same as the using method in the first embodiment above in operations [1] to [3] and operations [7] and [8], but is different from the using method in the first embodiment in operations [4] to [6]. Here, the different operations will be described.

[4'] After the operation [3] described above, the medical tube assembly 1 with the implant 8 inserted in the medical tube 2B is prepared. As aforementioned, the distal portion 81 of the implant 8 is protruding from the distal end opening 21 of the medical tube 2B.

After a connected state is established, the puncture member 3 is rotated clockwise in FIG. 15, as shown in the figure. By this rotation, the puncture member 3 is pulled out of the piercing hole 500, and, this time, the medical tube assembly 1 (medical tube 2B) is inserted into and passed through the piercing hole 500. In accordance with an exemplary embodiment, the medical tube assembly 1 is in a state where its distal-side portion is protruding from the body surface 600 on the side of the obturator foramen 400b, whereas its proximal-side portion is protruding from the body surface 600 on the side of the obturator foramen 400a. Even in this state, the distal portion 81 of the implant 8 is protruding from the distal end opening 21 of the medical tube 2B.

[5'] Next, as shown in FIG. 16, the puncture member 3 of the puncture apparatus 10 is taken away from the body surface 600 together with the support member 20.

[6'] Subsequently, as depicted in FIG. 17, with the distal portion 81 of the implant 8 grasped by one hand, then, keeping this state, a proximal portion of the medical tube 2B is grasped by the other hand, and the proximal portion is drawn proximally until the medical tube 2B is pulled out of the piercing hole 500. As a result, the implant 8 is left inserted in and passed through the piercing hole 500.

Thereafter, the operations [7] and [8] can be carried out sequentially.

Note that while in the medical tube 2B the distal portion 81 of the implant 8 is preliminarily set protruding from the distal end opening 21, this is not restrictive. The distal portion 81 can be set retracted to the depth side from the distal end opening 21. In this case, in accordance with an exemplary embodiment, it can be preferable for the medical tube 2B, for example, to be so configured that its distal portion is separable. Such a configuration can help ensure that upon separation of the distal portion, the distal portion 81 of the implant 8 protrudes from the medical tube 2B. By separating the distal portion after the operation [5'], then, the operation [6'] can be carried out or performed in a relatively assured manner.

While the medical tube, medical tube assembly and puncture needle according to the present disclosure have been described above referring to the embodiments shown in the drawings, the present disclosure is not limited to the embodiments. Each of the components of the medical tube, medical tube assembly and puncture needle can be replaced with one of an arbitrary configuration that is able to function in an equivalent manner. In addition, arbitrary structures or configurations can be added to the aforementioned.

Each of the medical tube, the medical tube assembly and the puncture needle disclosed here can be a combination of arbitrary two or more configurations (features) of the above embodiments.

While in the above embodiments the bent region of the medical tube maintains its state of being bent in an arc shape by its own rigidity, this is not restrictive. The bent state of the bent region can be maintained, for example, by a method in which a rigid stylet or the like having a bent region bent in an arc shape is inserted in the medical tube.

Furthermore, the separation portion of the medical tube can include a perforation.

The medical tube according to the present disclosure is a medical tube in which to insert an elongated implant. The medical tube is composed essentially of a tube having a distal end opening where the tube is open at its distal end, and a proximal end opening where the tube is open at its proximal end. The tube has a bent region where an intermediate portion in the longitudinal direction of the tube is bent and the bent state is maintained. The tube also has a connection portion which is provided near the proximal end opening and to which a puncture needle having a sharp needle tip at its distal end is connected from the needle tip side. By use of the medical tube, therefore, an operation of inserting an implant into a living body and indwelling the implant inside the living body can be carried out relatively easily and reliably.

Accordingly, the medical tube assembly according to the present disclosure has industrial applicability.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A medical tube assembly comprising:
   a puncture needle configured to form an arc-shaped puncture hole in a living body, the arc-shaped puncture hole passing between a urethra and a vagina, the puncture needle having a needle tip at a distal end of the puncture needle, the puncture needle having a tapered portion, wherein an outside diameter of the puncture needle increases along a proximal direction from the needle tip; and
   a tube configured to have an elongated implant inserted in the tube and inserted into the arc-shaped puncture hole, the tube comprising:
      a connection portion having a proximal end opening where the tube is open at a proximal end of the tube;
      a bent region distal of the connection portion, the bent region being bent in an arc shape, and wherein the tube is rigid at least in the bent region;
      the connection portion being configured to connect to the puncture needle from a needle tip side;
   the tube having a length longer than a length of the puncture needle; and
   wherein the bent region extends from the connection portion to a distal end of the tube.

2. The medical tube assembly according to claim 1, wherein the connection portion comprises:
   at least one slit that penetrates a tube wall of the tube, and bending a portion surrounded by the at least one slit toward an inner side of the tube.

3. The medical tube assembly according to claim 1, wherein the connection portion comprises:
   a reduced-diameter part where the tube has a reduced inner diameter.

4. The medical tube assembly according to claim 1, comprising:
   a separation portion permitting the tube to be separated at an intermediate position in a longitudinal direction of the tube.

5. The medical tube assembly according to claim 4, wherein the separation portion is located at a central portion in a longitudinal direction of the bent region.

6. The medical tube assembly according to claim 5, comprising:

a marker for grasping a position of the central portion in the longitudinal direction of the bent region.

7. The medical tube assembly according to claim 4, wherein the tube is separated by virtue of the separation portion into a first tube on a distal side and a second tube on a proximal side, and
the separation portion is a fitting structure in which a proximal portion of the first tube fits in a distal portion of the second tube before the tube is separated into the first tube and the second tube.

8. The medical tube assembly according to claim 1, wherein at least a portion on a distal side of the tube has a relatively flat cross-sectional shape as compared with the connection portion.

9. The medical tube assembly according to claim 8, wherein a thickness direction of the flat cross-sectional shape is oriented towards a center of the bent region.

10. The medical tube assembly according to claim 1, comprising:
a lumen opening into the proximal end opening of the tube, and wherein the implant is configured to be inserted in the lumen.

11. The medical tube assembly according to claim 1, wherein the connection portion comprises:
a cutout on a proximal side of the needle tip of the puncture needle.

12. The medical tube assembly according to claim 1, wherein the puncture needle has a reduced outside diameter and the connection portion has a reduced-diameter part where the puncture needle is reduced in outside diameter at a position immediately on a proximal side of the needle tip of the puncture needle.

13. The medical assembly according to claim 1, wherein the length of the tube is configured to extend from an inguinal region on one side of a body surface to an inguinal region on an other side of the body surface in the arc-shaped puncture hole in the living body.

14. The medical assembly according to claim 1, wherein the connection portion is rigid.

15. The medical assembly according to claim 1, wherein the connection portion is flexible.

16. A medical tube assembly comprising:
a puncture needle configured to form an arc-shaped puncture hole in a living body, the arc-shaped puncture hole passing between a urethra and a vagina, the puncture needle having a needle tip at a distal end of the puncture needle, the puncture needle having a tapered portion, wherein an outside diameter of the puncture needle increases along a proximal direction from the needle tip;
a medical tube configured to be inserted in the arc-shaped puncture hole, the medical tube having a proximal end opening where the medical tube is open at a proximal end of the tube, a connection portion near the proximal end opening and to which the puncture needle is connected from a needle tip side, a bent region distal of the connection portion, the bent region being bent in an arc shape, and wherein the medical tube is rigid at least in the bent region, and wherein the medical tube has a length longer than a length of the puncture needle;
an elongated implant configured to be inserted in the medical tube;
the bent region extending from the connection portion to a distal end of the tube; and
wherein the length of the tube is configured to extend from an inguinal region on one side of a body surface to an inguinal region on an other side of the body surface in the arc-shaped puncture hole in the living body.

17. The medical tube assembly according to claim 16, wherein the connection portion comprises:
at least one slit that penetrates a tube wall of the tube, and bending a portion surrounded by the at least one slit toward an inner side of the tube; and
the connection portion includes a reduced-diameter part wherein the tube has a reduced inner diameter.

18. The medical tube assembly according to claim 16, comprising:
a separation portion permitting the tube to be separated at an intermediate position in a longitudinal direction of the tube, and wherein the separation portion is located at a central portion in a longitudinal direction of the bent region; and
a marker for grasping a position of the central portion in the longitudinal direction of the bent region.

* * * * *